United States Patent [19]
Shafer et al.

[11] Patent Number: 5,523,281
[45] Date of Patent: Jun. 4, 1996

[54] METHOD OF ACCELERATING AND PROLONGING FLOWERING IN PLANTS

[75] Inventors: Warren E. Shafer, Libertyville; Derek D. Woolard, Waukegan; Rolland D. Carlson, Barrington; Candace L. Black-Schafer, Libertyville, all of Ill.

[73] Assignee: Abbott Laboratories, Abbott Park, Ill.

[21] Appl. No.: 196,081

[22] PCT Filed: Oct. 16, 1992

[86] PCT No.: PCT/US92/08915

§ 371 Date: Feb. 17, 1994

§ 102(e) Date: Feb. 17, 1994

[87] PCT Pub. No.: WO93/07746

PCT Pub. Date: Apr. 29, 1993

[51] Int. Cl.$^6$ .................................................. A01N 37/44
[52] U.S. Cl. ............................................ 504/320; 504/351
[58] Field of Search ............................................... 504/320

[56] References Cited

U.S. PATENT DOCUMENTS

| | | | |
|---|---|---|---|
| 3,928,406 | 12/1975 | Leeper et al. | 71/88 |
| 4,059,431 | 11/1977 | Takematsu et al. | 71/87 |
| 4,441,918 | 4/1984 | Rehberg | 71/113 |
| 4,554,017 | 11/1985 | Schröder et al. | 71/113 |
| 4,744,811 | 5/1988 | Schulz et al. | 71/6 |

OTHER PUBLICATIONS

Bernier et al. "Physiological Signals That Induce Flowering." *The Plant Cell.* 5:1147–1155. Oct. 1993.
M. S. Reid, Greenhouse Grower, "Keep Pot Plants from Shattering" Dec. 1986, pp. 66–67.
Greenhouse Manager, 26 (Nov. 1989) "Pot Plants–STS Spray Keeps Bud Drop Away".
Hormonal Regulation and Development, 1980, MacMillian, pp. 317–336 41.6 Ethylene et seq.
HortScience, 15(3) Jun. 1980, Yang, "Regulation of Ethylene Biosynthesis" pp. 238–243.
Briggs, et al., Ann. Rev. Plan Physiol. 1984, 35:155–89.

*Primary Examiner*—S. Mark Clardy
*Attorney, Agent, or Firm*—Jerry F. Janssen

[57] ABSTRACT

Treatment of cotton plants or flowering ornamental plants with a formulation comprising an agent effective to inhibit 1-aminocyclopropane-1-carboxylic acid synthase activity accelerates the flowering of cotton plants and accelerates and extends flower longevity of flowering ornamental plants, particularly when such flowering plants are subjected to the stresses of the conditions of shipping. A preferred agent is L-trans-2-amino-4-(2-aminoethoxy)-3-butenoic acid (AVG) or a salt thereof:

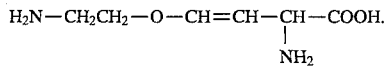

10 Claims, No Drawings

METHOD OF ACCELERATING AND PROLONGING FLOWERING IN PLANTS

This application has been filed under 35 USC371 from PCT/US92/08915, filed Oct. 16, 1992.

TECHNICAL FIELD

The present invention relates to methods of accelerating flowering and prolonging flower longevity in plants. More particularly, the present invention concerns a method for accelerating flowering in cotton and ornamental plants and prolonging flower longevity in ornamental plants by applying a formulation comprising an agent which inhibits 1-aminocyclopropane- 1-carboxylic acid synthase activity.

BACKGROUND OF THE INVENTION

Cotton is an important international commercial crop. It is estimated that over sixteen million acres of cotton are in production worldwide, with the 1988 worldwide production of cotton exceeding 26.1 million bales. The commercial production of cotton, as with most commercial crops, is affected by many factors not within the control of the grower. Total crop volume and timing of crop maturation are subject to the vagaries of weather as well as other factors and can be effectively controlled by the grower only by choice of planting time, the use of fertilizers, etc. There is thus a need for methods of more effectively managing crop rotation, timing of crop maturation, and crop production volume.

Similarly, the marketing of cut flowers and ornamental flowering plants is of considerable economic importance to the horticultural industry. In 1989 the total wholesale market for cut flowers, flowering plants and foliage and bedding plants amounted to approximately 2.43 billion dollars. The sale of cut flowers contributed approximately 459 million dollars to this total, and the sale of potted flowering plants contributed approximately 522 million dollars.

The marketing of these products generally involves shipping from the site where the flowers are grown to commercially important markets elsewhere in the country. The handling, packaging and shipping of both cut flowers and plants places stresses upon both which can result in damage, diminishing their commercial value to the retailer.

While methods and materials are known for protecting cut ornamental flowers from stress damage caused by shipping, the problem of protecting ornamental flowering plants from shipping damage has not been adequately addressed in the prior art. The stresses placed on cut flowers by shipping often results in early senescence (wilting) which can be due, in part, to the effects of ethylene. Ethylene gas, either produced by the plant itself in response to stress, or in the environment causes early senescence. Ethylene is known to be involved in a number of plant processes including senescence. A number of chemicals which limit ethylene-induced damage to cut flowers have been identified. These include silver thiosulfate, carboxymethoxylamine (also known as aminooxyacetic acid AOAA), L-trans-2-amino-4-(2-aminoethoxy)-3-butenoic acid (AVG), rhizobitoxine, and L-trans-2-amino-4-methoxy-3-butenoic acid (MVG). Silver thiosulfate is believed to inhibit the effect of external ethylene, while the others are believed to act internally to inhibit the ability of the cut flowers to themselves produce ethylene.

The use of silver thiosulfate for the prevention of shipping stress damage to flowering plants has been suggested (see, for example, Michael S. Reid, *Greenhouse. Grower*, pp. 66–67, December, 1986 and the *Greenhouse Manager* of November 1989 (p. 26). The use of silver salts on potted plants has not been officially approved and the proper disposal of silver salts is a subject of environmental concern. There is thus a need for effective and environmentally compatible agents for use in protecting flowering plants during shipping.

SUMMARY OF THE INVENTION

It has been found, in accordance with the present invention, that the application of formulations comprising an effective amount of an agent which inhibits aminocyclopropylcarboxylic acid (known by the acronym "ACC") synthase activity to cotton and certain ornamental flowering plants both accelerates and promotes the flowering process. Moreover, the application of such formulations to ornamental flowering plants prolongs bloom life. Particularly effective ACC synthase inhibiting agents of the method of the present invention are L-trans-2-amino- 4-(2-aminoethoxy)-3-butenoic acid (also known as aminoethoxyvinylglycine or "AVG"), carboxymethoxylamine (also known as aminooxyacetic acid or "AOAA"), rhizobitoxine, and L-trans-2-amino-4-methoxy-3-butenoic acid (also known as methoxyvinyl glycine or "MVG"). AVG is preferred agent preferred in the method of the present invention.

DETAILED DESCRIPTION

In one embodiment, the present invention provides a method of accelerating and promoting budding and blooming of cotton plants. By "accelerating" budding and blooming is meant the production of buds on cotton plants at an earlier stage in plant development when the method of this invention is employed than occurs when the method is not employed. "Promotion" of flowering is used to mean increasing the total number of buds and flowers in cotton plants treated with the method of this invention compared with untreated cotton plants.

In this method, the ACC synthase inhibitor composition, preferably comprising AVG, is applied to the cotton plants early in the development of the flower buds (called "squares" in the art). Preferably; the ACC synthase inhibitor composition is applied when the squares are small, of a size resembling a match head. At this stage of development, the growing cotton flower buds are called "match head squares." The ACC synthase inhibitor composition is applied to the budding cotton plants by spraying to run-off, with repeated optional applications by the same method, preferably at roughly weekly intervals. One or two applications following the initial application at the match head square stage are preferred for optimal acceleration of blooming. Compositions having concentrations of AVG ranging between 10 ppm and 2000 ppm may be used, with concentrations ranging between about 125 ppm to about 1000 ppm being preferred.

In another embodiment of the method of the present invention, flower senescence of potted ornamental plants during shipping may be prevented. Current practice in the industry is to "sleeve" commercial potted plants, pack them into shipping canons, and surface ship the sleeved and boxed plants in refrigerated trucks or rail cars to their destination. While cut flowers are often air-shipped, surface shipment is almost always the only commercially feasible means for shipping potted plants because of the additional weight of the pot and soil. Some commercial flowering plants such as miniature carnations (*Dianthus sp.*) which are grown on the East and West coasts of the United States are not sold in the midwest because the damage to the plants caused by the stresses of shipment destroy the commercial value of the plants at the destination. The method of the present invention provides a means of protecting such plants from early senescence and permits their shipment to heretofore unavailable markets while also unexpectedly accelerating the flowering process.

The method of the present invention is not limited, however, to use in protecting potted flowering ornamental plants from shipping damage. The method is also applicable, for example, to the acceleration of flowering in floral crops which are grown for sale as cut flowers. In this application, the method can be used by commercial wholesale florists to harvest flower crops earlier. In addition, the beneficial effects, e.g. the increase in flower longevity, accompanying the application of the compositions of this invention to the flowering plant carry over to the cut flowers following harvesting.

The formulations of this invention are generally applied to plants by either spraying the foliage, buds, and flowers or by "drenching." When applied by spraying, the formulations are sprayed on the plants, preferably to the point of runoff, by techniques well known to the art. In this method it is preferred, although not necessarily required, that the formulations contain an anionic or non-ionic surfactant to aid in thoroughly wetting the foliage, buds, and flowers with the formulations. In the drenching method, the formulation is poured into the soil surrounding the plant or can be applied to the roots from below as, for example, in the technique known as "ebb-and-flow" where water and nutrients are applied to growing plants in a greenhouse bench from below. In the drenching technique, a surfactant is typically not included in the formulation.

The formulations themselves comprise an inhibitor of ACC synthase activity, or a salt thereof, present in a liquid medium in concentrations ranging between about 10 parts per million (ppm) and 2000 parts per million (ppm), with concentrations near the lower end of this range being preferred when the formulations of the present invention are applied to flowering plants by the "drenching" method (see below). When the formulations are applied to flowering plants by spray techniques, concentrations ranging between about 100–1000 ppm are preferred. The formulations may also include an anionic or non-ionic surfactant, particularly if the intended use involves spray application of the formulations to the plants. The liquid medium is preferably aqueous, but may include or consist essentially of an organic solvent which is not detrimental to the plants.

The ACC synthase activity inhibitor is selected from the group carboxymethoxyl-amine (AOAA), L-trans-2-amino-4-(2-aminoethoxy)-3-butenoic acid (AVG), rhizobitoxine, and L-trans-2-amino-4-methoxy-3-butenoic acid (MVG), with AVG being preferred.

Suitable non-ionic surfactant materials useful for the purposes of this invention include, but are not necessarily limited to nonionic surfactants which are partial esters of common fatty acids (e.g. palmitic, stearic and oleic acids) with hexitol anhydrides (hexitans and herxides) derived from sorbitol. These materials are commercially available under the tradename Span® from The Pierce Chemical Co., P.O. Box 117, Rockford, IL 61105. Other suitable nonionic surfactants include materials derived from surfactants of the Span® type by etherification of the free hydroxyl groups with poly(oxyethylene) groups. This latter class of surfactants is available under the Tradename Tween® (ICI Americas, Wilmington, DE). Additionally, polyethoxylated octyl- or nonylphenols (commercially marketed under the tradename Triton® ) can also be used. Preferred nonionic surfactants for use in the process of this invention include Tween® 20, Tween® 80, and Triton X-405. Suitable anionic suffactants include alkali metal salts of esters of sulfosuccinic acid such as sodium dioctyl sulfosuccinate, marketed under the tradename Areosol OT®(American Cyanamid, Wayne, NJ).

The formulations are typically prepared by dissolving the ACC synthase activity inhibitor in the liquid medium, preferably water, and subsequently adding and dissolving the surfactant (if needed), and diluting the mixture to the final desired concentration. The following examples are representative of the results achieved with the method of this invention.

EXAMPLE 1

Acceleration and Promotion of Flowering in Cotton
(cv. DPL 90) Evaluation of Time of Application To determine the best treatment regimen for application of the ACC synthase inhibitor to accelerate floweing in cotton plants, compositions containing 250 ppm of AVG and 0.05 weight percent Tween® 20 were applied to fifteen cotton plants (cultivated variety DPL 90). Treatment solutions were prepared by dissolving AVG in water, followed by addition of a surfactant (Tween® 20). The compositions were applied to groups of fifteen cotton plants for each application regimen by spraying the foliage and buds of the plants to runoff. In the "one spray" group, the 15 plant group was treated once at the match head square stage of development and received no further treatment prior to evaluation. In the "two spray" group, the 15 plant group was treated once at the match head square stage, followed by one additional treatment one week later. In the "three spray" group, the 15 plant group was treated once at the match head square stage, followed by two successive treatments at one week intervals thereafter.

Once the foliage had dried following each application, the plants were held in a greenhouse for continued growth and evaluation. The total number of squares (flower buds) for each 15-plant group were counted each week for seven weeks after spraying. The total of each column is equivalent to integration of a curve which plots number of squares (flower buds) on the ordinate versus time on the abscissa and is indicative of the total flowering in each 15-plant group, whether control or treated. The data appear in Table 1.

TABLE 1

| Week Following First Application | Tween ® 20 Control (Number of Squares) | One Spray (Number of Squares) | Two Sprays (Number of Squares) | Three Sprays (Number of Squares) |
| --- | --- | --- | --- | --- |
| 0 | 30 | 24 | 9 | 13 |
| 1 | 94 | 66 | 49 | 62 |
| 2 | 167 | 118 | 127 | 120 |
| 3 | 223 | 183 | 189 | 187 |
| 4 | 265 | 256 | 311 | 308 |
| 5 | 195 | 241 | 282 | 278 |

TABLE 1-continued

| Week Following First Application | Tween ® 20 Control (Number of Squares) | One Spray (Number of Squares) | Two Sprays (Number of Squares) | Three Sprays (Number of Squares) |
| --- | --- | --- | --- | --- |
| 6 | 75 | 114 | 123 | 137 |
| 7 | 5 | 31 | 27 | 33 |
| Total | 1054 | 1033 | 1117 | 1138 |

The data in Table 1 show that application of AVG formulations to budding cotton plants promotes flowering, and that repeated applications are more effective than a single application. The total number of squares (flower buds) over the duration of the experiment increases from that of control for each application regimen, from one spray to three sprays.

EXAMPLE 2

Acceleration and Promotion of Flowering in Cotton (cv. Acala SJ2) Evaluation of AVG Concentration (125–500 ppm)

To evaluate the effect of varying concentrations of AVG on acceleration and promotion of blooming in cotton plants, AVG compositions comprising 125, 250, and 500 ppm of AVG were applied to groups of 15 plants at each concentration. Treatment solutions were prepared by dissolving AVG in water, followed by addition of a surfactant (Tween® 20) to prepare solutions containing 125, 250 or 500 ppm of AVG and 0.05 weight percent Tween® 20. Groups of 15 cotton plants (cultivated variety Acala SJ2) were sprayed to runoff with each composition and with a control solution containing just the surfactant using the "three spray" application regimen of Example 1; that is, each plant group was sprayed to runoff with the compositions at the match head aquare (plus ten days) stage of development and twice thereafter at weekly intervals. When the foliage had dried following each application, the plants were held in a greenhouse for continued growth and evaluation.

The total number of squares (flower buds) in each 15-plant group were counted each week for five weeks following the initial application. The data are presented in Table 2. As is the data presented in Table 1, the integrated total number of squares (flower buds) is tabulated.

TABLE 2

| Week Following First Application | Tween ® 20 Control (Number of Squares) | 125 ppm AVG (Number of Squares) | 250 ppm AVG (Number of Squares) | 500 ppm AVG (Number of Squares) |
| --- | --- | --- | --- | --- |
| 0* | 69 | 86 | 67 | 81 |
| 1* | 84 | 93 | 93 | 93 |
| 2* | 70 | 112 | 96 | 103 |
| 3 | 48 | 58 | 81 | 93 |
| 4 | 29 | 54 | 42 | 78 |
| 5 | 5 | 17 | 10 | 50 |
| Total | 305 | 420 | 389 | 498 |

*Compositions were applied to the plants.

Examination of the data in Table 2 clearly shows that application of AVG to the plants accelerated and promoted the formation of squares (flower buds) and, more particularly, that the effects were more pronounced at the higher concentration of AVG composition.

EXAMPLE 3

Acceleration and Promotion of Flowering in Cotton (cv. Acala SJ2) Evaluation of AVG Concentration (250–1000 ppm)

Since an increase in promotion and acceleration of flowering in cotton plants was observed in Example 2 with increasing concentration of AVG, the procedure of Example 2 was repeated with AVG compositions of 250, 500, and 1000 ppm AVG, each containing 0.05 weight percent Tween® 20. In this example, the total number of squares (flower buds) for each 15-plant group was counted each week for seven weeks following the initial application. As above, the integrated total number of squares (flower buds) over the duration of the experiment is also tabulated. The results are presented in Table 3.

TABLE 3

| Week Following First Application | Tween ® 20 Control (Number of Squares) | 250 ppm AVG (Number of Squares) | 500 ppm AVG (Number of Squares) | 1000 ppm AVG (Number of Squares) |
| --- | --- | --- | --- | --- |
| 0 | 16 | 20 | 18 | 14 |
| 1 | 18 | 22 | 21 | 17 |
| 2 | 59 | 71 | 84 | 87 |
| 3 | 112 | 129 | 160 | 170 |
| 4 | 145 | 138 | 187 | 217 |
| 5 | 135 | 118 | 159 | 180 |
| 6 | 64 | 60 | 79 | 88 |
| 7 | 15 | 13 | 17 | 25 |
| Total | 564 | 571 | 725 | 798 |

The data in Table 3 show that there is acceleration of flowering in cotton plants following treatment with AVG, with an increase in acceleration with increasing concentration of the AVG composition applied. There is a pronounced increase in the total number of squares (flower buds) over control at the higher concentrations (500 ppm and 1000 ppm) of AVG used in the applications.

EXAMPLE 4

Acceleration and Promotion of Flowering in Cotton (cv. Acala SJ2) Evaluation of AVG Concentration (250–1000 ppm)

In addition to tabulating the integrated total number of squares (flower buds) over the duration of the experiment, in the experiment described in Example 4, the cumulative number of cotton flowers actually present on plants in each 15-plant group at each point in time during the course of the experiment was observed. These data appear in Table 4.

TABLE 4

| Day Following First Application | Tween® 20 Control (Number of Blossoms) | 250 ppm AVG (Number of Blossoms) | 500 ppm AVG (Number of Blossoms) | 1000 ppm AVG (Number of Blossoms) |
|---|---|---|---|---|
| 5 | 5 | 6 | 4 | 6 |
| 10 | 13 | 10 | 13 | 10 |
| 15 | 16 | 17 | 18 | 14 |
| 20 | 41 | 44 | 54 | 43 |
| 25 | 74 | 80 | 100 | 90 |
| 30 | 112 | 115 | 142 | 140 |
| 35 | 145 | 149 | 181 | 202 |

The data in Table 4 show that at Day 25 and thereafter, the cumulative numbers of actual blossoms present in the treated groups of plants were higher than for the control group, with the effect being more pronounced with increasing concentration of AVG, indicating the promotion-of flowering which results in cotton plants using the method of the present invention.

EXAMPLES 5–8

Evaluation of Promotion and Acceleration of Flowering in Several Cultivated Varieties of Dianthus, sp.)

Treatment solutions were prepared by dissolving AVG in water, followed by addition of a surfactant (Tween® 20). Potted miniature carnations were sprayed to the point of run-off either with a control solution of surfactant only (Tween®, 0.05 percent by weight) or AVG (1000 ppm) and Tween® 20 (0.05% by weight). To simulate conditions under which the plants are commercially shipped and distributed, the plants were sleeved at about 24 hours after treatment, boxed and held under refrigeration conditions (about 5° C.) for 7–10 days. After this time, the potted plants were unboxed and placed in a greenhouse for evaluation. The number of viable and dead flowers on each plant were then counted and recorded. The results are presented in Table 5.

TABLE 5

| Example Plant (Cultivated Variety) Days Following Treatment | Control Plants Treated with 0.05% Tween® 20 | | Treated Plants Treated with 1000 ppm AVG + 0.05% Tween® 20 | |
|---|---|---|---|---|
| | Average Number of Viable Flowers | Average Number of Dead Flowers | Average Number of Viable Flowers | Average Number of Dead Flowers |
| Example 5 Miniature Carnations ('Show Girl') | | | | |
| 7 | 8 | 0 | 9 | 0 |
| 12 | 20 | 1 | 23 | 0 |
| 16 | 27 | 6 | 35 | 2 |
| 21 | 31 | 14 | 43 | 10 |
| 26 | 37 | 24 | 49 | 21 |
| Example 6 Miniature Carnations ('Pink Dancer') | | | | |
| 7 | 13 | 0 | 14 | 1 |
| 12 | 24 | 3 | 24 | 2 |
| 16 | 31 | 5 | 35 | 3 |
| 21 | 39 | 11 | 47 | 7 |
| 26 | 44 | 21 | 52 | 21 |
| Example 7 Miniature Carnations ('Tiny Dancer') | | | | |
| 7 | 7 | 0 | 9 | 0 |
| 12 | 13 | 3 | 16 | 3 |
| 16 | 18 | 4 | 21 | 3 |
| 21 | 24 | 10 | 27 | 7 |
| 26 | 27 | 15 | 32 | 14 |
| Example 8 Miniature Carnations ('Kopo Kardinal') | | | | |
| 7 | 3 | 0 | 4 | 0 |
| 12 | 9 | 0 | 13 | 0 |
| 16 | 16 | 0 | 22 | 0 |
| 21 | 21 | 2 | 35 | 4 |
| 26 | 26 | 5 | 42 | 8 |

EXAMPLE 9

In Example 5, potted miniature carnations, cv. Lindsey, were sprayed to the point of run-off and subsequently sleeved, boxed, and stored under refrigeration, as in Examples 1–4, however, using a solution containing 2000 ppm AVG and 0.05% by weight of Tween® 20 or control (0.05% Tween® 20). Other than the higher concentration of AVG, the protocol for Example 5 was identical to that used in Examples 1–4. The results of Example 5 appear in Table 6.

TABLE 6

| Example Plant (Cultivated Variety) Days Following Treatment | Control Plants Treated with 0.05% Tween® 20 | | Treated Plants Treated with 2000 ppm AVG + 0.05% Tween® 20 | |
|---|---|---|---|---|
| | Average Number of Viable Flowers | Average Number of Dead Flowers | Average Number of Viable Flowers | Average Number of Dead Flowers |
| Example 9 Miniature Carnations ('Lindsey') | | | | |
| 15 | 3 | 2 | 5 | 1 |
| 19 | 5 | 2 | 6 | 2 |
| 20 | 5 | 2 | 8 | 2 |
| 23 | 7 | 4 | 12 | 3 |
| 30 | 4 | 8 | 12 | 8 |

EXAMPLE 10

Treatment solutions were prepared by dissolving AVG in water followed by addition of a surfactant (Tween® 20). Rooted geranium cuttings, cv. Red Satisfaction were sprayed to the point of run-off either with a control solution of surfactant only (Tween®, 0.05 percent by weight) or AVG (125 ppm) and Tween® 20(0.05% by weight). To simulate conditions under which the plants are commercially distributed, the plants were boxed at about 24 hours after treatment and held under refrigeration conditions (about 5° C.) for 7–10 days. After this time, the potted plants were unboxed and placed in a greenhouse for evaluation. The total number of viable and dead flowers on each plant were then counted and recorded. The results are presented in Table 7.

TABLE 7

| Example Plant (Cultivated Variety) Days Following Treatment | Control Plants Treated with 0.05% Tween® 20 | | Treated Plants Treated with 125 ppm AVG + 0.05% Tween® 20 | |
|---|---|---|---|---|
| | Average Number of Viable Flowers | Average Number of Dead Flowers | Average Number of Viable Flowers | Average Number of Dead Flowers |
| Example 10 Geraniums ('Red Satisfaction') | | | | |
| 7 | 0 | 0 | 0 | 0 |
| 17 | 0 | 0 | 3 | 0 |
| 19 | 0 | 0 | 7 | 0 |
| 22 | 0 | 0 | 9 | 2 |
| 26 | 1 | 0 | 8 | 3 |
| 38 | 28 | 10 | 15 | 28 |

Examination of the data appearing in Tables 5–7 shows that the method of the present invention promotes flowering, extends the longevity of the resulting flowers and also unexpectedly accelerates the flowering process in ornamental plants.

The examples presented above are illustrative of the method of the present invention and are not to be viewed as limiting the scope of the invention as defined by the appended claims.

What is claimed is:

1. A method of accelerating flowering in plants comprising administering to said plants a formulation comprising an effective amount of a 1-aminocyclopropane-1-carboxylic acid synthase activity inhibitory agent L-trans-2-amino-4-(2-aminoethoxy)-3-butenoic acid.

2. The method of claim 1 wherein said 1-amino-cyclopropane-1-carboxylic acid synthase activity inhibitory agent is L-trans-2-amino-4-methoxy-3-butenoic acid or a salt thereof.

3. The method of claim 2 wherein said formulation comprises from about 10 pans per million to about 2000 parts per million of said L-trans-2-amino-4-methoxy-3-butenoic acid or a salt thereof.

4. The method of claim 1 wherein said formulation further comprises between about 0.025 percent by weight to about 0.5 percent by weight of an anionic or a nonionic surfactant.

5. The method of claim 1 wherein said formulation is applied to the the leaves, buds and flowers of the plants.

6. The method of claim 1 wherein said formulation is applied to the roots of the plants.

7. A method of accelerating blooming in cotton plants comprising one or more applications to the foliage and buds of said cotton plants a composition comprising between about 10 ppm and about 2000 ppm of L-trans-2-amino 4-(2-aminoethoxy)-3-butenoic acid or a salt thereof.

8. The method of claim 7 wherein said composition is first applied to said cotton plants at the match head square stage of budding.

9. A method of accelerating and prolonging flowering in ornamental plants comprising one or more applications to the foliage, buds and flowers of said plants of a composition comprising between about 10 ppm and about 2000 ppm of L-trans-2-amino-4-(2-aminoethoxy)-3-butenoic acid or a salt thereof.

10. The method of claim 9 wherein said ornamental plants are members of the genus Dianthus.

* * * * *